(12) United States Patent
Ortmann et al.

(10) Patent No.: US 7,767,861 B2
(45) Date of Patent: Aug. 3, 2010

(54) METHOD FOR PRODUCING TRIVALENT ORGANOPHOSPHORUS COMPOUNDS

(75) Inventors: Dagmara Ortmann, Recklinghausen (DE); Klaus-Diether Wiese, Haltern am See (DE); Oliver Moller, Recklinghausen (DE); Dirk Fridag, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 278 days.

(21) Appl. No.: 10/584,148

(22) PCT Filed: Oct. 29, 2004

(86) PCT No.: PCT/EP2004/052729

§ 371 (c)(1), (2), (4) Date: Jun. 22, 2006

(87) PCT Pub. No.: WO2005/063776

PCT Pub. Date: Jul. 14, 2005

(65) Prior Publication Data

US 2007/0112219 A1     May 17, 2007

(30) Foreign Application Priority Data

Dec. 23, 2003 (DE) .................... 103 60 771

(51) Int. Cl.
*C07F 9/02* (2006.01)
(52) U.S. Cl. .............. 568/10; 568/12; 568/14
(58) Field of Classification Search ........... 556/404; 558/83
See application file for complete search history.

(56) References Cited

U.S. PATENT DOCUMENTS

| | | | |
|---|---|---|---|
| 4,769,498 A | 9/1988 | Billig et al. | |
| 4,885,401 A * | 12/1989 | Billig et al. | 568/454 |
| 5,093,534 A | 3/1992 | Ludwig et al. | |
| 5,734,072 A * | 3/1998 | Kleiner | 558/96 |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,331,657 B1 | 12/2001 | Kaizik et al. | |
| 6,403,836 B2 | 6/2002 | Kaizik et al. | |
| 6,403,837 B1 | 6/2002 | Hess et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Röttger et al. | |
| 6,627,782 B2 | 9/2003 | Kaizik et al. | |
| 6,680,414 B2 | 1/2004 | Knoop et al. | |
| 6,720,457 B2 | 4/2004 | Drees et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,109,346 B2 | 9/2006 | Beller et al. | |
| 2002/0111487 A1 * | 8/2002 | Roettger et al. | 546/22 |
| 2003/0144559 A1 | 7/2003 | Hess et al. | |
| 2003/0195368 A1 | 10/2003 | Rottger et al. | |
| 2004/0138508 A1 * | 7/2004 | Tinge et al. | 568/454 |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2005/0043279 A1 | 2/2005 | Selent et al. | |
| 2005/0171371 A1 | 8/2005 | Borner et al. | |
| 2005/0182277 A1 | 8/2005 | Totsch et al. | |
| 2005/0209455 A1 | 9/2005 | Boerner et al. | |
| 2005/0209489 A1 | 9/2005 | Moller et al. | |
| 2005/0234270 A1 | 10/2005 | Kaizik et al. | |
| 2005/0256281 A1 | 11/2005 | Grund et al. | |
| 2006/0036121 A1 | 2/2006 | Kaizik et al. | |
| 2006/0089469 A1 | 4/2006 | Komarov et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0183936 A1 | 8/2006 | Grass et al. | |

(Continued)

FOREIGN PATENT DOCUMENTS

DE     19 03 356     9/1969

(Continued)

OTHER PUBLICATIONS

Gatrone et L., The synthesis and purification of the carbamoylmethylphosphine oxides, Solvent Extraction and Ion Exchange (1987), 5(6), 1075-116.*

(Continued)

*Primary Examiner*—Daniel M Sullivan
*Assistant Examiner*—Chukwuma O Nwaonicha
(74) *Attorney, Agent, or Firm*—Oblon, Spivak, McClelland, Maier & Neustadt, L.L.P.

(57) ABSTRACT

The present invention relates to a process for preparing organophosphites, organophosphonites and organophosphinites by condensing phosphorus trihalides or organophosphorus halides with organic compounds bearing hydroxyl groups in the presence of polymeric basic ion exchange resins.

Figure 1:
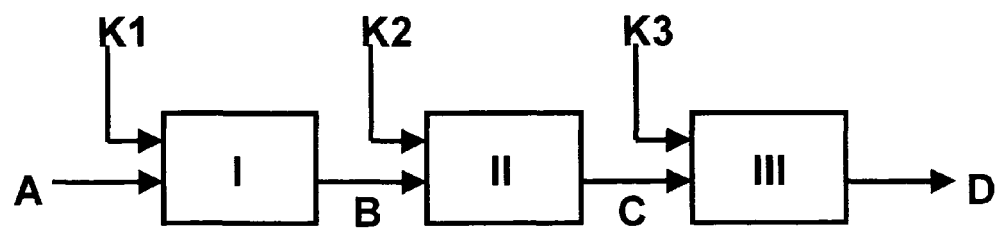

The process according to the invention makes possible in a simple manner the preparation of trivalent organophosphorus compounds which may be used, for example, as ligands in rhodium complexes which may be used as a catalyst in hydroformylation.

17 Claims, 1 Drawing Sheet

U.S. PATENT DOCUMENTS

2007/0149781 A1 6/2007 Riermeier et al.
2007/0197799 A1 8/2007 Holz et al.

FOREIGN PATENT DOCUMENTS

| EP | 0 213 639 | 3/1987 |
|---|---|---|
| EP | 1 201 675 | 5/2002 |
| WO | 95/14659 | 6/1995 |

OTHER PUBLICATIONS

Martin, Facile reduction in the synthesis of phosphorylcholine affinity columns, Tettrahedron Letters, 37, No. 44, pp. 7921-7924, 1996.*
Gatrone et al., The synthesis and purification of the carbamoylmethylphosphine oxides, Solvent Extraction and Ion Exchange (1987), 5(6), 1075-116.*
U.S. Appl. No. 11/574,063, filed Feb. 22, 2007, Nierlich, et al.
U.S. Appl. No. 11/494,741, filed Jul. 28, 2006, Kaizik, et al.
U.S. Appl. No. 10/562,454, filed Aug. 18, 2006, Krissmann, et al.
U.S. Appl. No. 10/576,302, filed Apr. 19, 2006, Kaizik, et al.
U.S. Appl. No. 10/588,762, filed Aug. 8, 2006, Wiese, et al.
U.S. Appl. No. 09/708,646, filed Nov. 9, 2000, Hess, et al.
U.S. Appl. No. 10/505,879, filed Sep. 3, 2004, Borgmann.
U.S. Appl. No. 10/593,330, filed Sep. 19, 2006, Borgmann, et al.
U.S. Appl. No. 10/584,492, filed Jun. 22, 2006, Ortmann, et al.
U.S. Appl. No. 10/525,376, filed May 8, 2006, Moeller, et al.
Martin, Lenore M. et al., "Facile Reduction in the Synthesis of Phosphorylcholine Affinity Columns", Tetrahedron Letter, vol. 37, No. 44, pp. 7921-7924, 1996.
Lot, Olivier et al., "New electron-deficient aminophosphonite-phosphite ligands for asymmetric hydroformylation of styrene", Journal of Molecular Catalysis A: Chemical, vol. 164, pp. 125-130, 2000.
U.S. Appl. No. 12/065,091, filed Feb. 28, 2008, Hess, et al.
U.S. Appl. No. 11/908,343, filed Sep. 11, 2007, Holz, et al.
U.S. Appl. No. 12/515,967, filed May 22, 2009, Selent, et al.
U.S. Appl. No. 12/594,602, filed Oct. 5, 2009, Selent, et al.

* cited by examiner

METHOD FOR PRODUCING TRIVALENT ORGANOPHOSPHORUS COMPOUNDS

The present invention relates to a process for preparing organophosphites, organophosphonites and organophosphinites by condensing phosphorus trihalides or organophosphorus halides with organic compounds bearing hydroxyl groups in the presence of polymeric basic ion exchange resins.

Owing to their broad field of application, organophosphorus compounds have gained considerable industrial importance. They are used, for example, as plasticizers, flame retardants, UV stabilizers and antioxidants. In addition, they constitute important intermediates in the preparation of fungicides, herbicides, insecticides and pharmaceuticals. Accordingly, a large number of preparative processes has been developed. Particularly important among the organophosphorus compounds is the substance class of organophosphites. One review of the preparative methods for organophosphites is by K. Sasse and can be found in "Methoden der Organischen Chemie" [Methods of Organic Chemistry] (Houben-Weyl), Volume XII/2, Chapter 1, Thieme Verlag, Stuttgart (1964) and L. Maier, G. Kosolapoff, "Organic Phosphorus Compounds", Volume 4, John Wiley & Sons, p. 255-462 and the literature references contained therein.

The preparation of triaryl phosphites by reacting phosphorus trihalides with suitable phenols succeeds in the presence of a catalyst in an inert solvent at temperatures of from 150 to 200° C. (DE 20 28 878, DE 20 07 070). The hydrogen chloride which is formed is distilled off in situ. This process has a series of disadvantages. In order to bring about the in situ distillation of the hydrogen chloride, high temperatures are necessary. Especially at elevated temperature, hydrogen chloride is extremely corrosive and therefore requires the use of special materials in the plant construction. In addition, the reaction times are very long, which has the consequence of a high fraction of by-products and therefore costly and inconvenient purification of the crude product.

It is therefore often industrially more advantageous to condense phosphorus trihalides, monoaryl dichlorophosphites or halodiaryl chlorophosphites with phenols in the presence of basic compounds which scavenge the hydrogen chloride being formed. The bases used are usually nitrogen compounds, for instance trialkylamines (DD 301615, U.S. Pat. No. 4,415,686, JP 54030140), dimethylformamide (JP 10053595, EP 511156), N,N-dialkylanilines or nitrogen heterocycles such as pyridine (G. Kosolapoff, "Organophosphorus Compounds", John Wiley & Sons (1950), p. 184). Other processes employ alkali metal and/or alkaline earth metal hydroxides (EP 0032202). JP 54030140 describes the condensation of phosphorus trihalides with phenols in the presence of substoichiometric amounts of amines, ammonium salts, carboxylic acids, guanidines, amides, amidines, sulfones and phosphines.

The document WO 91/09040 describes the preparation of sterically hindered triaryl phosphites starting from the corresponding phenols and phosphorus trihalide in the presence of mercaptothiazoles and dithiocarbamic acid derivatives.

A review of the synthetic methods of organophosphonites is given, for example, in Houben-Weyl, "Methoden der Organischen Chemie", XII/1, p. 44 ff. A review of the methods for the synthesis of organophosphinites is given in Houben-Weyl, "Methoden der Organischen Chemie", XII/1, p. 210 ff.

One disadvantage of the known industrial processes is the removal of the base and/or its reaction products or of the catalysts in the workup of the crude organophosphorus product. A distillative separation is often possible only with difficulty or even impossible as a consequence of the low vapor pressures of the components involved. When a solid base is used and/or the reaction products of the base occur in solid form or a precipitation of the base and/or its reaction products is possible, a removal from the crude product may be effected by filtration or sedimentation. On the industrial scale, especially in a continuous procedure, these separating operations are known to be extremely costly and inconvenient in the industrial construction and operation. They are sensitive toward changes in the operating parameters and/or type and properties of the substances to be separated. In general, it is also necessary to use large amounts of solvent, for example in order to wash product or value from the filtercake. However, this often succeeds only incompletely (U.S. Pat. No. 5,710,307).

When tertiary amines, especially triethylamine, are used, the trialkylammonium halides which precipitate out lead to a sharp increase in the viscosity of the reaction mixture and to the formation of wall deposits. Under these conditions, stirring and heat exchange are considerably complicated. In order to counter this disadvantage, the document EP 1 234 831 proposes relatively long-chain tertiary amines such as tri-n-propylamine, triisopropylamine, tri-n-butylamine, triisobutylamine and tri-tert-butylamine. Nevertheless, the fundamental disadvantages of filtration mentioned above remain on the industrial scale.

A further workup of the crude organophosphorus products may be effected by methods known to those skilled in the art, for example by (fractional) crystallization, sublimation, precipitation or chromatographic methods, in some cases also by distillation or rectification. The use of these separating methods on the industrial scale is also associated with a high level of technical complexity and expense.

The document EP 0 285 136 claims a process for purifying tertiary organophosphites to free them of pentavalent organophosphorus compounds which are by-produced in the synthesis or are formed as degradation or hydrolysis products of the tertiary organophosphites. The process envisages a treatment of the dissolved impure organophosphite with water at elevated temperature in the presence of a Lewis base. Useful Lewis bases are inorganic salts (carbonates, hydroxides, oxides), tertiary amines and polymers which bear amine groups.

However, the synthesis of the organophosphorus compounds themselves is not addressed. One disadvantage of the claimed process is the treatment with water. Not only the impurities to be removed but also the tertiary organophosphites themselves react under the given conditions, so that, depending on the hydrolysis stability of the organophosphites, a portion of the product of value is lost.

DE 100 53 272 describes the preparation of diphosphites in which one phosphite unit has a salicylic acid building block. DE 100 58 383 describes the preparation of phosphinines which have at least two phosphorus atoms. DE 101 14 868 describes the preparation of diphosphines.

DE 101 40 083 and DE 101 40 072 describe the preparation of diphosphites in which both phosphite units have a salicylic acid building block. DE 101 400 86 describes the preparation of monophosphites which have a salicylic acid building block. DE 102 10 918 describes the preparation of diphosphites in which at least one phosphite likewise has a salicylic acid building block. All of the aforementioned documents describe the use of tertiary amines, especially of triethylamine, pyridine or N-methylpyrrolidinone, in the reaction of phosphorus halides with alcohols.

The existing processes have one or more of the following disadvantages:

a) The complete removal of the base used from the target product is costly and inconvenient.
b) The salts, formed in the reaction, of the bases used are frequently voluminous or occur in a particle size distribution which complicates the removal by filtration.
c) The maintenance of the desired reaction temperature is difficult owing to the high exothermicity.

It is therefore an object of the present invention to provide a simple process for preparing trivalent organophosphorus compounds which does not have one or more of these disadvantages.

It has been found that, surprisingly, this object can be achieved by preparing trivalent organic phosphorus compounds which have at least one P—O bond by reacting a trivalent phosphorus compound in which at least one halogen atom is bonded to the phosphorus atom with an organic compound which has at least one OH group in the presence of an ion exchange resin.

This is surprising especially because, despite the use of a heterogeneous substrate to scavenge the hydrogen halide being formed, there were no losses in the yield.

The present invention therefore provides a process for preparing trivalent organophosphorus compounds by condensing phosphorus compounds of the formula i $$PHal_aR_{(3-a)} \quad (i)$$

where Hal=halide selected from chlorine, bromine and iodine and may be the same or different when a plurality of halides is present (a>1), R is an organic radical which is bonded to the phosphorus via a carbon or oxygen atom and preferably has at least 2, more preferably at least 3 carbon atoms, and, when a<2, the R radicals present may be the same or different, and a=from 1 to 3, with organic compounds which have at least one OH group, which comprises carrying out the reaction in the presence of at least one basic, especially weakly basic, ion exchange resin. i.e. ion exchangers which are present in the form of the free amine.

The process according to the invention has the following advantages over the conventional processes:
a) There are no saltlike by-products which can only be removed with difficulty from the target product.
b) The base used is in solid form and, despite reaction with the hydrogen halide, does not change its state of matter and substantially retains its size. The ion exchanger of the process according to the invention, typically present as a packing or beads, can be removed from the reaction mixture by the simplest means, for example by using coarse-mesh sieves matched to the size of the ion exchanger particles.
c) Adhesion of large amounts of product of value is prevented by the size and shape of the ion exchanger alone. The use of packings or particles of relatively large particle size makes the surface of the ion exchanger small relative to the volume compared to a precipitated base of the conventional type. Therefore, it is also necessary to use only small amounts of solvent in the process according to the invention in order to flush any adhering product of value off the surface of the consumed base.
d) When ion exchanger is used, the rate constant of the reaction is lower than when homogeneously dissolved bases are used. As a result, the exothermic reaction is easier to control.

e) During the reaction, no voluminous salts which, as a consequence of the rise in viscosity that they bring about, may cause concentration and temperature differences in the reaction mixture are formed.

The process according to the invention is described by way of example hereinbelow without the invention being restricted to these embodiments. Further variants which likewise form part of the subject matter of the present invention and whose field of application is evident from the description and the claims are evident to those skilled in the art.

In the process according to the invention for preparing trivalent organophosphorus compounds by condensing phosphorus compounds of the formula i $$PHal_aR_{(3-a)} \quad (i)$$

where Hal=halide selected from chlorine, bromine and iodine and may be the same or different when a plurality of halides is present (a>1), R is an organic radical which is bonded to the phosphorus via a carbon or oxygen atom and preferably has at least 2, more preferably at least 3 carbon atoms, and, when a<2, the R radicals present may be the same or different and may optionally be covalently joined together, and a=from 1 to 3, with organic compounds which have at least one OH group, the condensation reaction is carried out in the presence of at least one basic, especially weakly basic, ion exchange resin, i.e. ion exchangers which are present, for example, in the form of the free amine (not in the OH form).

The phosphorus compound of the formula i used is preferably at least one compound selected from the compounds of the following formulae

(0)

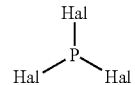

(1)

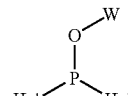

(2)

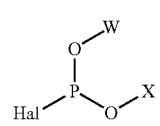

(4)

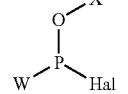

(6)

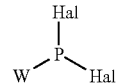

(7)

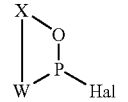

(9)

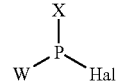

where Hal is halide, W and X are substituted or unsubstituted, aliphatic, alicyclic, aliphatic-alicyclic, heterocyclic, aliphatic-heterocyclic, aromatic-aromatic or aliphatic-aromatic hydrocarbons having from 1 to 50 carbon atoms, and W or X may be the same or different or covalently joined together. The substituted hydrocarbon radicals may have, for example, one or more substituents selected from primary, secondary and tertiary alkyl groups, alicyclic groups, aromatic groups, —N($R^5$)$_2$, —NH$R^5$, —NH$_2$, fluorine, chlorine, bromine, iodine, —CN, —C(O)—$R^5$, —C(O)H or —C(O)O—$R^5$, —CF$_3$, —O—$R^5$, —C(O)N—$R^5$, —OC(O)—$R^5$ and/or —Si($R^5$)$_3$, where $R^5$ is a monovalent hydrocarbon radical having from 1 to 20 carbon atoms, for example an alkyl radical, in particular methyl, ethyl, propyl or n-butyl or tert-butyl radical, or, for example, an aryl radical, in particular phenyl or naphthyl radical. When a plurality of hydrocarbon radicals $R^5$ is present, they may be the same or different.

The substituents are preferably restricted to those which have no influence on the reaction itself. Particularly preferred substituents may be selected from the halogens, for example chlorine, bromine or iodine, the alkyl radicals, for example methyl, ethyl, propyl, isopropyl, butyl, sec-butyl, t-butyl, neopentyl, sec-amyl, t-amyl, isooctyl, t-octyl, 2-ethylhexyl, isononyl, isodecyl and octadecyl, the aryl radicals, for example phenyl, naphthyl or anthracyl, the alkylaryl radicals, for example, tolyl, xylyl, dimethylphenyl, diethylphenyl, trimethylphenyl, triethylphenyl or p-alkylphenyl, the aralkyl radicals, for example benzyl or phenylethyl, the alicyclic radicals, for example cyclopentyl, cyclohexyl, cyclooctyl, cyclohexylethyl or 1-methylcyclohexyl, the alkoxy radicals, for example methoxy, ethoxy, propoxy, butoxy or pentoxy, the aryloxy radicals, for example phenoxy or naphthoxy, —OC(O)$R^5$ or —C(O)$R^5$, for example acetyl, propionyl, trimethylacetoxy, triethylacetoxy or triphenylacetoxy, and the silyl radicals having three hydrocarbon radicals (—Si(hydrocarbyl)$_3$, for example trimethylsilyl, triethylsilyl or triphenylsilyl.

Of the above-listed phosphorus trihalides and organophosphorus halides, preference is given to phosphorus trichloride and the organophosphorus chlorides.

When the compounds used in the process according to the invention have amine groups, i.e. —NH$_2$, —N($R^5$)$_2$ or —NH$R^5$, they have to function as a weaker base relative to the amine group of the ion exchanger in equilibrium reactions. Compounds which have amine groups and do not fulfill this condition cannot be used (directly) as reactants in the process according to the invention. One means of enabling the use of such compounds after all is to protect the appropriate groups in a known manner by incorporating protecting groups and, after carrying out the process according to the invention, removing the protecting group again.

The coupling component which has hydroxyl groups and may be used in the process according to the invention may be aliphatic, alicyclic, aliphatic-alicyclic, heterocyclic, aliphatic-heterocyclic, aromatic-aromatic, aliphatic-aromatic, compounds which have from 1 to 50 carbon atoms and one, two or more hydroxyl groups. For the preparation of monophosphorus compounds in the process according to the invention, compounds which only have one OH group are used exclusively. For the preparation of compounds having two or more phosphorus atoms, compounds are correspondingly used which have two or more OH groups.

The compound having at least one hydroxyl group which is used in the process according to the invention is preferably at least one substituted or unsubstituted compound selected from aliphatic alcohols having up to 19 carbon atoms, for example methanol, ethanol, n-propanol, isopropanol, 1-butanol, 2-butanol, t-butanol, 2-ethylhexanol, isononanol, isodecanol, isotridecanol, OH-substituted aromatic compounds, for example phenol and phenol derivatives, 1,4-dihydroxybenzene, 1,2-dihydroxybenzene, 1,8-dihydroxynaphthalene, 1,1'-binaphthyl 2,2'-diol or 2,2'-binaphthyl 1,1'-diol, di- or polyols, for example glycols, sugar, for example cyclodextrins, and the substituted compounds have substituents selected from primary, secondary and tertiary alkyl groups, alicyclic groups, aromatic groups, —N($R^5$)$_2$, —NH$R^5$, —NH$_2$, fluorine, chlorine, bromine, iodine, —CN, —C(O)—$R^5$, —C(O)H or —C(O)O—$R^5$, —CF$_3$, —O—$R^5$, —C(O)N—$R^5$, —OC(O)—$R^5$ and/or —Si($R^5$)$_3$, where $R^5$ is a monovalent hydrocarbon radical, preferably having from 1 to 20 carbon atoms. When a plurality of hydrocarbon radicals $R^5$ is present, they may be the same or different. The substituents are preferably restricted to those which have no influence on the reaction itself. Particularly preferred substituents may be selected from the halogens, for example chlorine, bromine or iodine, the alkyl radicals, for example methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, the aryl radicals, for example phenyl, naphthyl or anthracyl, the alkylaryl radicals, for example, tolyl, xylyl, dimethylphenyl, diethylphenyl, trimethylphenyl, triethylphenyl or p-alkylphenyl, the aralkyl radicals, for example benzyl or phenylethyl, the alicyclic radicals, for example cyclopentyl, cyclohexyl, cyclooctyl, cyclohexylethyl or 1-methylcyclohexyl, the alkoxy radicals, for example methoxy, ethoxy, propoxy, butoxy or pentoxy, the aryloxy radicals, for example phenoxy or naphthoxy, —OC(O)$R^5$ or —C(O)$R^5$, for example acetyl, propionyl, trimethylacetoxy, triethylacetoxy or triphenylacetoxy, and the silyl radicals having three hydrocarbon radicals (—Si($R^5$)$_3$, for example trimethylsilyl, triethylsilyl or triphenylsilyl.

The trivalent organophosphorus compound prepared by the process according to the invention is preferably at least one compound selected from the compounds of the following formulae

(1)

(2)

(3)

(3a)

(4)

-continued

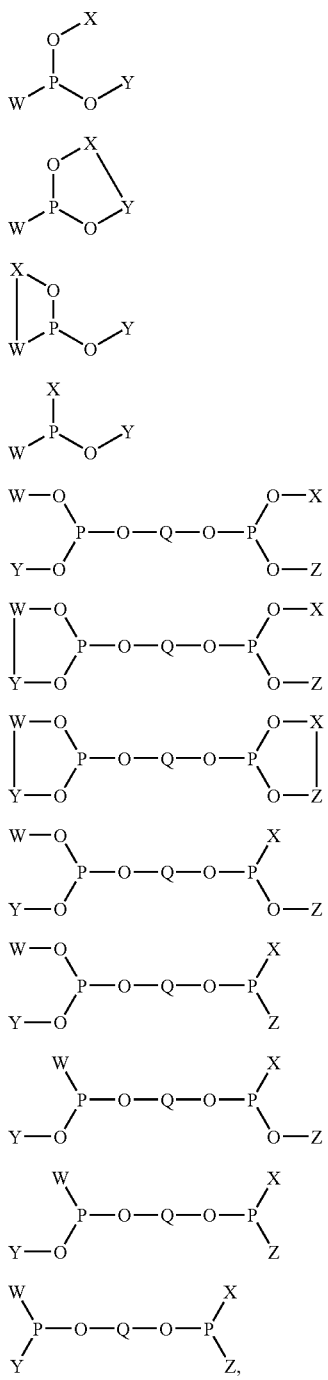

where W, X, Y and Z are each substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, and W, X, Y and Z are the same or different or covalently joined together, and where Q is an at least bivalent, substituted or unsubstituted, aliphatic, alicyclic, aliphatic-alicyclic, heterocyclic, aliphatic-heterocyclic, aromatic, aromatic-aromatic or aliphatic-aromatic hydrocarbon radical. The substituted hydrocarbon radicals may have one or more substituents selected from primary, secondary and tertiary alkyl groups, alicyclic groups, aromatic groups, —N(R$^5$)$_2$, —NHR$^5$, —NH$_2$, fluorine, chlorine, bromine, iodine, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical, preferably having from 1 to 20 carbon atoms. When a plurality of hydrocarbon radicals R$^5$ is present, they may be the same or different. The substituents are preferably restricted to those which have no influence on the reaction itself. Particularly preferred substituents may be selected from the halogens, for example chlorine, bromine or iodine, the alkyl radicals, for example methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, the aryl radicals, for example phenyl, naphthyl or anthracyl, the alkylaryl radicals, for example, tolyl, xylyl, dimethylphenyl, diethylphenyl, trimethylphenyl, triethylphenyl or p-alkylphenyl, the aralkyl radicals, for example benzyl or phenylethyl, the alicyclic radicals, for example cyclopentyl, cyclohexyl, cyclooctyl, cyclohexylethyl or 1-methylcyclohexyl, the alkoxy radicals, for example methoxy, ethoxy, propoxy, butoxy or pentoxy, the aryloxy radicals, for example phenoxy or naphthoxy, —OC(O)R$^5$ and —C(O)R$^5$, for example acetyl, propionyl, trimethylacetoxy, triethylacetoxy or triphenylacetoxy, and the silyl radicals having three hydrocarbon radicals (—Si(hydrocarbyl)$_3$, for example trimethylsilyl, triethylsilyl or triphenylsilyl.

The process according to the invention enables in particular the preparation of dihalophosphites 1, monohalophosphites 2 or triorganophosphites 3 and 3a by condensing dihalophosphites 1, monohalophosphites 2 and phosphorus trihalides with mono- or poly-OH-substituted organic compounds, i.e. organic compounds having OH groups.

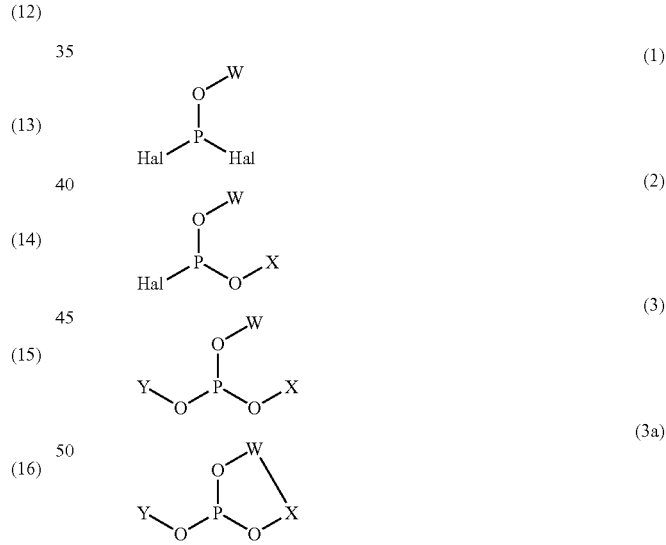

In the structures, W, X and Y are each as defined above. W, X and Y are preferably each aliphatic, alicyclic, aliphatic-alicyclic, heterocyclic, aliphatic-heterocyclic, aromatic-aromatic, aliphatic-aromatic, hydrocarbon radicals having from 2 to 25 carbon atoms. X, Y and W may be the same or different or be covalently joined together, as, for example, in structure 3a.

It is also possible by means of the process according to the invention to prepare halodiorganophosphonites 4, triorganophosphonites 5, 5a or 5b, by carrying out the condensation of dihaloorganophosphonites 6 or halodiorganophosphonites 4 or 7 with mono- or poly-OH-substituted organic compounds in the presence of basic ion exchange resins. In the structures, W, X and Y are each as defined above.

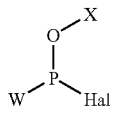
(4)

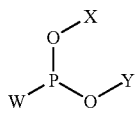
(5)

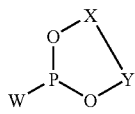
(5a)

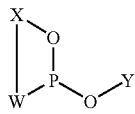
(5b)

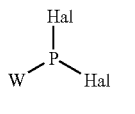
(6)

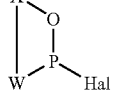
(7)

In a further process variant, the process according to the invention may be used to prepare triorganophosphinites 8 by condensing haloorganophosphinites 9 with mono- or poly-OH-substituted organic compounds in the presence of basic ion exchange resins.

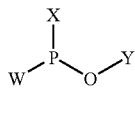
(8)

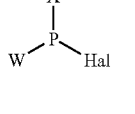
(9)

The process according to the invention may also be used to prepare bisphosphites of the structure 10, 10a or 10b by condensing di- or poly-OH-substituted hydrocarbons with diorganohalophosphites 2 in the presence of one or more basic ion exchange resins.

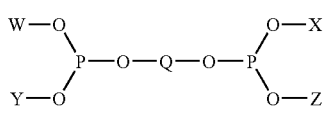
(10)

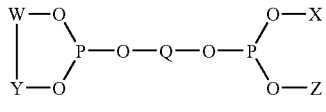
(10a)

-continued

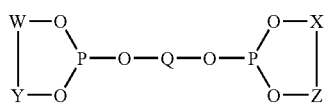
(10b)

It is possible by means of the process according to the invention, in a further variant, to prepare diphosphorus compounds of the phosphite-phosphonite type 12 by condensing di- or poly-OH-substituted hydrocarbons with diorganohalophosphites 2 and halodiorganophosphonites 4 in the presence of one or more basic ion exchange resins.

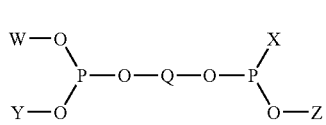
(12)

It is possible by means of the process according to the invention, in a further variant, to prepare diphosphorus compounds of the phosphite-phosphinite type 13 by condensing di- or poly-OH-substituted hydrocarbons with halophosphinites 9 and diorganohalophosphites 2 in the presence of one or more basic ion exchange resins.

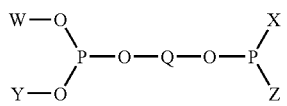
(13)

It is possible by means of the process according to the invention, in a further variant, to prepare diphosphonite compounds 14 by condensing di- or poly-OH-substituted hydrocarbons with halodiorganophosphonites 4 in the presence of one or more basic ion exchange resins.

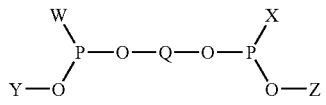
(14)

It is possible by means of the process according to the invention, in a further variant, to prepare compounds of the phosphonite-phosphinite type 15 by condensing di- or poly-OH-substituted hydrocarbons with halodiorganophosphonites 4 and haloorganophosphinites 9 in the presence of one or more basic ion exchange resins.

(15)

It is possible by means of the process according to the invention, in a further variant, to prepare diphosphinite compounds 16 by condensing di- or poly-OH-substituted hydrocarbons with haloorganophosphinites 9 in the presence of one or more basic ion exchange resins.

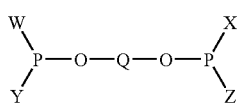

In the formulae 10 to 16, Q, W, X, Y and/or Z may each be as defined above. In particular, Q is a bivalent hydrocarbon radical which may be aliphatic, alicyclic, aliphatic-alicyclic, heterocyclic, aliphatic-heterocyclic, aromatic, aromatic-aromatic or aliphatic-aromatic, and be substituted or unsubstituted, and W, X, Y and Z are each aliphatic, alicyclic, aliphatic-alicyclic, heterocyclic, aliphatic-heterocyclic, aromatic-aromatic, aliphatic-aromatic hydrocarbon radicals having from 2 to 25 carbon atoms which may be unsubstituted or substituted, and X, Y, W and Z may be the same or different or be covalently joined together, as shown by way of example in formula 10a or 10b.

According to K. Sasse in "Methoden der Organischen Chemie" (Houben-Weyl), Volume XII/2, Chapter 1, p. 62 ff., Thieme Verlag, Stuttgart (1964) and G. M. Kosolapoff, "Organophosphorus Compounds", chap. 7, XV, pp. 139, John Wiley, New York (1950) and the literature references contained therein, the preparation of asymmetric organophosphites and asymmetric phosphonites succeeds by stepwise reaction of the organophosphorus halides or phosphorus halides used as starting substances with compounds containing hydroxyl groups in the presence of amines. Depending on the desired target compound, the process according to the invention may comprise one or more reaction steps, and the reaction of in each case one compound having at least one phosphorus-halogen bond with a compound having at least one hydroxyl group is one reaction step. Accordingly, the process according to the invention may be performed as a multistage process for preparing asymmetric organophosphites and asymmetric phosphonites, in which case the reaction steps are each carried out in the presence of a (weakly) basic ion exchanger.

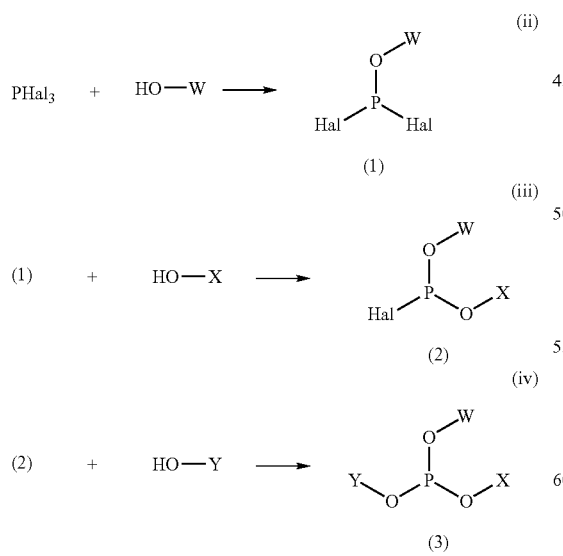

As illustrated in the formulae ii, iii and iv, it is possible, starting from a phosphorus trihalide, by reacting with one equivalent of a compound containing one hydroxyl group HO—W, to prepare an organophosphorus dihalide, by reacting the organophosphorus dihalide with a further equivalent of a compound containing one hydroxyl group HO—X, to prepare a diorganophosphorus halide, and, by reacting further with one equivalent of a compound containing one hydroxyl group HO—Y, finally preparing an asymmetric triorganophosphite. In the preparation of asymmetric phosphonites, an analogous procedure according to the formulae v and vi may be employed.

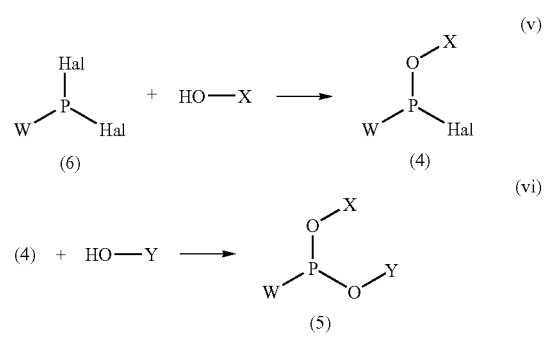

In the following formulae vii and viii, the inventive stepwise preparation of a diphosphorus compound is shown using the example of a bisphosphite 10. A dihydroxyl compound 22 is reacted with one equivalent of a halodiorganophosphite 2 to give the compound 23 which is finally reacted with one further equivalent of a halodiorganophosphite to give the bisphosphite 10. The halodiorganophosphites mentioned may be the same or different, so that symmetric or asymmetric bisphosphites are obtained.

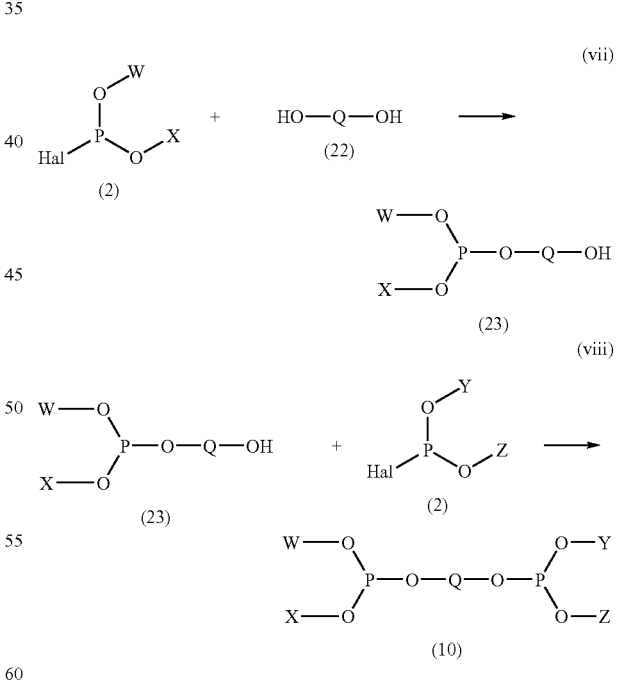

In the formulae ii to viii, W, X, Y, Z and Q are each as defined above.

According to the formulae vii and viii, dihydroxyl compounds 22 may be reacted with diorganophosphites 2, halodiorganophosphonites 4 or 7, haloorganophosphinites 9. In two reaction steps, asymmetric diphosphorus compounds may be prepared, such as bisphosphites 10, phosphite-phosphonite compounds 12, phosphite-phosphinite compounds 13, bisphosphonites 14, phosphonite-phosphinite compounds 15 and bisphosphinites 16. In the case of the same organophosphorus halides, the preparation of the symmetric diphosphorus compounds may of course be effected in one process step. When the reactivities of the two organophosphorus halides toward dihydroxyl compounds 22 are sufficiently different, the preparation of asymmetric diphosphorus compounds may likewise be carried out in one process step. Otherwise, one process step has to be provided for each reaction step.

In a similar manner to the reactions vii and viii, compounds which bear more than two phosphorus units may be prepared by reacting compounds which have three or more hydroxyl groups stepwise with organophosphorus halides.

When a compound which still contains one or more hydroxyl groups, for example a compound of the structure 23, is the target of the preparation, the reaction sequence may be terminated at this stage. Complete conversion of the hydroxyl groups is not necessary.

The reaction steps illustrated in reaction schemes ii to viii may be carried out batchwise. In this case, one coupling component is initially charged together with one or more ion exchange resins and the second coupling component is subsequently metered in. The feed of the components or feed of solvent may be used in some cases to control the heat production rate or the temperature in the reaction mixture. In the batchwise method, it is important for a very high yield of desired product to initially charge and meter in the correct coupling component. For example, in the case of the selective preparation of asymmetric organophosphorus compounds of the formulae 1, 2, 3, 3a, 4, 5, 5a, 5b or 8 according to schemes ii to vi, preference is given to initially charging the phosphorus compound, i.e. the phosphorus halide or the organophosphorus halide together with one or more basic ion exchange resins and subsequently metering in the compound having an OH group (hydroxyl component). In the case of the selective preparation of asymmetric diphosphorus compounds according to schemes vii and viii, preference is given to initially charging the component having OH groups together with one or more ion exchange resins and subsequently metering in the organophosphorus halides.

After each process step, but also after each reaction step, the crude product may be worked up and reacted further in the next reaction step. However, it may also be more advantageous, after the complete conversion of one coupling component, to directly add the next component and to dispense with the workup between the two reaction steps. In the context of the present invention, the reaction of in each case one compound having at least one phosphorus-halogen bond with a compound having at least one hydroxyl group should be regarded as one reaction step.

The reaction time in the individual reaction steps may be the same or different, but in each case sufficiently long in order to achieve the desired conversion. The reaction temperatures in the individual reaction steps may be the same or different. The basic ion exchange resin or resins used in the individual reaction steps may be the same or different.

The reactors used for batchwise reaction control may be stirred tanks. The basic ion exchange resin or resins may be used in the reaction mixture, for example, as freely mobile beads. It is also possible to combine the ion exchange resin or resins in the form of packages to which the convection stream of the stirrer flows. It is likewise possible to use spinning basket stirrers. In addition, the reactor systems used may be stirred reactors having full recycling (loop reactors). The flow to the ion exchange resin bed may be from above or below.

In another preferred embodiment of the process according to the invention, the reaction steps shown in schemes ii to viii may also be carried out continuously in reaction spaces connected in series. Such a reaction sequence is illustrated in FIG. 1: the reactant A and the first coupling component K1 are conducted into a first reaction stage I. The effluent of the first reaction stage B is subsequently, like a second coupling component K2 too, conducted into a second reaction stage II. It is also possible that the coupling components K mentioned are effluents of one continuous, or of a plurality of continuous, reactors which are optionally connected in series, i.e. are reactor sequences of the type outlined in FIG. 2 in parallel and converging connection.

In order to achieve a very high yield of the desired product in the preparation of asymmetric products, the concentration ratio of the reactants is to be appropriately set in each stage by the ratios of the particular feeds. Typically, equimolar or approximately equimolar amounts are set.

The residence time of the reactants in the individual reaction steps may also be the same or different in the continuous mode, but it has to be sufficient in each case in order to achieve the desired conversion in the particular stage. The basic ion exchange resin or resins used in the individual reaction steps may be the same or different.

The reactors used for continuous reaction control may be continuous stirred tanks. The basic ion exchange resin or resins may be used in the reaction mixture as freely mobile beads. It is also possible to combine the ion exchange resin or resins in the form of packages to which the convection stream of the stirrer flows. It is likewise possible to use spinning basket stirrers. In addition, tubular reactors may be used. The flow to the ion exchange resin bed may be from above or below. In the continuous reactors, partial recycling of the reactor effluents may be advantageous. In the case of the arrangement of continuous reactors in a reactor battery, the recycled fraction of the effluent of one reaction stage may be partly or fully recycled into the same stage, partly or fully conducted to the start of the preceding stage or partly or fully conducted to the start of the first stage of the first reactor of the reactor battery.

Quite generally, and irrespective of whether the process is carried out continuously or batchwise, when a plurality of reaction steps is carried out, identical or different ion exchangers may be used in the reaction steps. Equally, when a plurality of reaction steps is carried out, identical or different reaction conditions, in particular temperatures, may be set in the reaction steps. The temperatures selected in the reaction stages depend substantially upon the reactivity of the feedstocks and may, within a sequence of reactors, be the same or different. The temperature preferably rises within a reactor battery. The reaction temperatures are preferably from −50° C. to 150° C., preferably from −10° C. to 120° C. and more preferably from 20° C. to 100° C. As already described, the temperature may be controlled by the feed control of the components. It is equally possible to keep the temperature at a certain temperature by the use of heatable/coolable reactors. It is also possible to combine both measures for temperature regulation. In this way, quasi-isothermal operation of the entire process or of individual process or reaction steps is possible, which makes possible particularly exact setting to the optimum reaction temperature which can lead to better yields.

The process according to the invention is preferably carried out in the presence of a solvent or of a plurality of solvents. The selection of the solvent depends upon the solubility of the feedstocks. In addition, the solvent has to be substantially inert toward the feedstocks under the reaction conditions. The solvent may also be added to the reaction mixture to control the temperature. Preference is given to using solvents which may function as proton carriers.

Preferred solvents are, for example, aromatics such as benzene, chlorobenzene, toluene or xylenes, open-chain or cyclic alkanes such as pentane, n-hexane, n-heptane, cyclohexane or methylcyclohexane, open-chain or cyclic ethers such as diethyl ether, diisopropyl ether, methyl tert-butyl ether, anisole, tetrahydrofuran, 1,4-dioxane, 1,3-dioxolane, esters such as ethyl acetate, isobutyl acetate, tert-butyl acetate, cyclic carbonic esters such as ethylene carbonate, propylene carbonate and 1,2-butylene carbonate, ketones such as acetone, 2-butanone, 3,3-dimethyl-2-butanone, aromatic and aliphatic nitriles such as benzonitrile, propionitrile and acetonitrile, lactones, pyrrolidones, e.g. N-methylpyrrolidone, formamides, e.g. dimethylformamide, sulfoxides, e.g. dimethyl sulfoxide, and also N-alkylmorpholines and sulfolane. It is of course also possible to use mixtures of these solvents.

A particularly preferred embodiment of the process according to the invention is carried out in the presence of a proton transferrer which is preferably present in homogeneous form in the reaction mixture or reaction solution. The proton transferrers used may be bases, in particular amines, which are weaker bases than the weakly basic ion exchangers. The proton transferrers used are preferably those compounds which, in addition to the function as a proton transferrer, may also assume the function of the solvent. Such compounds may be, for example, N-methylpyrrolidone or methylimidazole. The use of a proton transferrer which is homogeneously distributed in the reaction mixture may increase the reaction rate, since the reaction is promoted by the reactants no longer having to come into contact directly with the ion exchanger, but rather only with the weaker base which is, though, homogeneously distributed in the reaction mixture. In the reaction mixture, there is preferably a molar ratio of proton transferrer to the free base provided by the ion exchanger of from 0.0001:1 to 1:1, preferably from 0.001 to 0.01.

Preference is given to carrying out the process according to the invention in the presence of one or more polymeric, (weakly) basic ion exchange resins, preferably based on styrene-divinylbenzene copolymers, in order to scavenge the hydrogen halide formed in the condensation of phosphorus trihalides or organophosphorus halides with organic compounds bearing hydroxyl groups. Particular preference is given to using ion exchange resins based on styrene-divinylbenzene copolymers which bear N,N-dialkylamine groups, for example N,N-dimethylamino groups. It is possible to use macroreticular ion exchange resins or those of the gel type. Particular preference is given to using macroreticular ion exchange resins.

Very suitable for use in the process according to the invention are commercially available (weakly) basic ion exchange resins, for example Lewatit MP62, DOWEX M-43 or Amberlyst A21.

Preference is given to using the ion exchanger in the form of particles, preferably having an average particle size of from 10 μm to 2 mm, more preferably from 0.1 to 1.5 mm, or in the form of a fixed package.

In the process according to the invention, at least sufficient weakly basic ion exchanger is used that for each mole of acid which is released in the compound formation or formations, at least one mole of free base is available on the ion exchanger. Preference is given to using sufficient ion exchanger that the ratio of moles of acid resulting from the release to moles of free base released by the ion exchanger is from 1:1 to 3:1, preferably from 1.1: to 2:1.

Before it is used in the process according to the invention, the ion exchange resin is preferably dried by known techniques, for example by heat treatment under reduced pressure (G. Mohorcic, M. Pregelj, M. Pirs, Ion Exchange and Membranes (1975), 2(2), 107-110, C. Buttersack, K. Struss, H. Widdecke, J. Klein, Reactive Polymers, Ion Exchangers, Sorbents (1987), 5(2), 171-180) or by azeotropic distillation with suitable azeotroping agents (GB 1120402).

To carry out the process in continuous or quasi-continuous mode, at least two parallel reactors are provided per reaction step or process step and are connected in such a way that when the ion exchanger is exchanged, regenerated or dried in one of the reactors, the reaction can be continued in the other reactor.

In order to the keep the costs of the process low, it is appropriate to regenerate the ion exchange resin laden with hydrogen halide (to bring it into the basic form) and reuse it. Weakly basic ion exchangers are regenerated with typically $NH_4OH$, $Na_2CO_3$ or NaOH. Precise instructions on this subject are provided by manufacturer's technical information sheets (for example Lewatit-Selective ion exchangers, Instructions for laboratory trials with Lewatit selective ion exchange resins, Technical Information, Bayer; Dow Liquid Separations, Dowex Marathon WBA, Ion Exchange Resin, Engineering Information, The Dow Chemical Company; Dowex Ion Exchange Resins, Properties, Impurities and Concentrations of Regenerant Chemicals).

Further information on the regeneration of ion exchangers can be found, for example, in: Regeneration of Anion Exchange Resins with Regular-Grade Diaphragm-Cell Caustic Soda: A Five-Year Plant Trial (IWC Proceedings, 10(88, S. D. Coker, M. P. Murphy); Petrochemical Company Anion Exchange Resin Regeneration Trial (Dow Report, August 1989, Michael A. Smith) and Caustic Soda for Ion Exchange Resin Regeneration (Marketing Research Report, April 1986, Ralph A. Bacon).

The present invention is illustrated in detail with reference to the figures FIG. 1 and FIG. 2 without the invention, whose scope of application is evident from the description and the claims, being restricted to these embodiments.

FIG. 1 shows one possible connection of reactors for a continuous mode. The process of FIG. 1 has three reaction steps. In the first step, a reactant A, for example a phosphorus trichloride, is fed into a reactor I which has an ion exchanger. Component K1 which is a first compound having an OH group is likewise metered into this reactor. The amount of component K1 is preferably such that there is a molar ratio of A to K1 of 3:1. The monoorganophosphorus dichloride obtained as the product B of the first reaction step I is transferred to the reactor II of the next reaction step which likewise has an ion exchanger. Also metered into this reactor is the component K2 which is a second compound having an OH group. The amount of component K2 is preferably in turn such that there is a molar ratio of B to K2 of 2:1 on entry into the reactor. The diorganophosphorus chloride obtained as the product C of the second reaction step II is transferred to the reactor III of the next reaction step which likewise has an ion exchanger. Also metered into this reactor is the component K3 which is a third compound having an OH group. The amount of component K3 is preferably such that there is a molar ratio of C to K3 of 1:1 on entry into the reactor. The product D obtained from reactor III is in the present case a phosphite.

Figure 2:
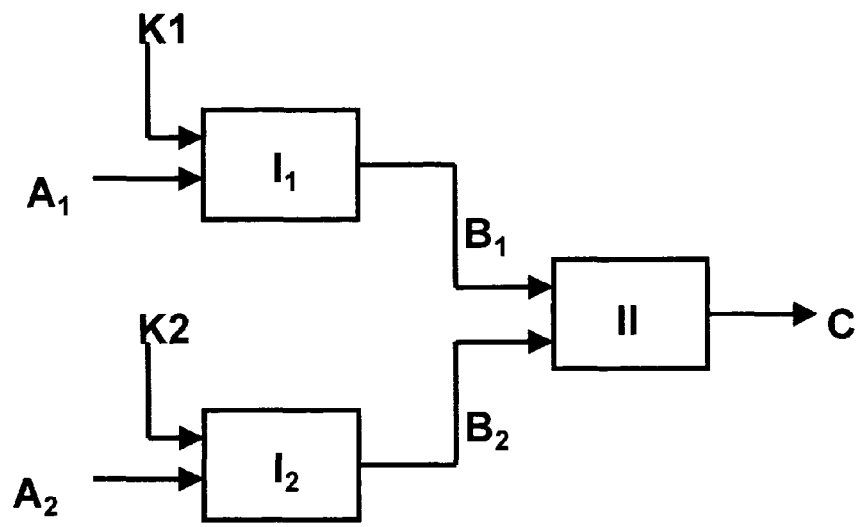

FIG. 2 shows another possible connection of reactors in which one process variant of the process according to the invention which has a plurality of reaction steps can be carried out continuously. Thus, the reactant A1, for example a halodiorganophosphite of the formula 2, is fed together with the component K1, for example a dihydroxyl compound of the formula 22, in a ratio of 1:1, into reactor II which has an ion exchanger. The reaction product $B_1$ obtained is a reaction product of the formula 23. The reactant $A_2$, for example a dihaloorganophosphite of the formula 1, is fed together with the component K2, for example an alkyl compound having an OH group, in a ratio of 1:1, into reactor 12 which likewise has an ion exchanger. The reaction product $B_2$ obtained is a product of the formula 2. The products $B_1$ and $B_2$ are conducted together, preferably in a molar ratio of 1:1, into the reactor II which likewise has an ion exchanger. In this reactor, the products $B_1$ and $B_2$ react to give product C of the formula 10 with elimination of hydrogen halide.

The examples which follow are intended exclusively to illustrate the invention but not restrict its scope of application which is evident exclusively from the description and the claims.

EXAMPLES

All preparations were carried out under protective gas using standard Schlenk technology. The solvents were dried before use over suitable desiccants. The ion exchanger used, Lewatit MP-62, was suspended in hexane to remove water and the water was removed azeotropically in a Dean-Stark apparatus.

Example 1

Phosphite of the Formula I, Prepared from 2,2'-bis(3,5-di-tert-butyl)phenol and Phosphorus Trichloride

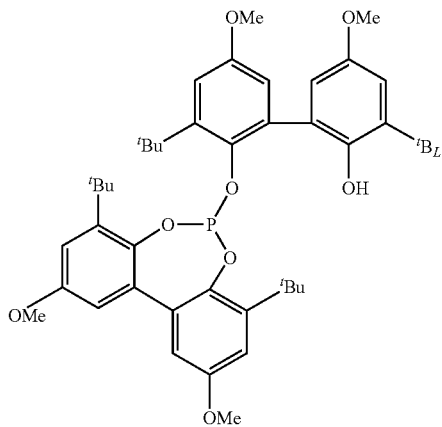

Example 1.1

Inventive

To a mixture of 26.5 g (0.045 mol eq.) of Lewatit MP-62 ion exchanger and 1.3 ml (2 g; 0.015 mol) of phosphorus trichloride in 200 ml of toluene was added dropwise at room temperature a solution of 12.3 g (0.03 mol) of 2,2'-bis(6-tert-butyl-1-hydroxy-4-methoxyphenol) in 100 ml of toluene. Subsequently, the reaction mixture was heated to 60° C. for 2 h and cooled overnight. For workup, the ion exchanger was filtered off by means of a glass frit and washed 4 times with 50 ml of toluene. The solution was freed of volatile constituents in an oil pump vacuum at room temperature and the product was dried under reduced pressure. Yield: 11.8 g, corresponding to 93% of theory.

Example 1.2

Prior Art According to EP 1 201 675

To a solution of 2.42 g of 2,2'-bis(6-tert-butyl-1-hydroxy-4-methoxyphenyl) (6.75 mmol) and 1.6 ml of pyridine in 22 ml of THF is added dropwise at 0° C. a solution of 0.93 g of $PCl_3$ (6.75 mmol) in 10 ml of THF. After stirring at 25° C. for 4 h. the solvent was removed under reduced pressure. After adding 40 ml of diethyl ether, filtering and concentrating under reduced pressure, 2.8 g (98%) of spectroscopically pure chlorophosphorous ester of 2,2'-bis(6-tert-butyl-1-hydroxy-4-methoxyphenyl) were obtained. 2.8 g of this chloroester (6.62 mmol) in 20 ml of THF were added at room temperature to a monolithium phenoxide solution, obtained at −20° C., from 2.37 g of 2,2'-bis(6-tert-butyl-1-hydroxy-4-methoxyphenyl) (6.62 mmol) in 30 ml of THF and 20.7 ml of a 0.32 M hexane solution of n-butyllithium (6.62 mmol). After 24 h, the mixture was concentrated under reduced pressure. Addition of 40 ml of methylene chloride, filtration and removal of the solvent under reduced pressure gave 4.6 g (93%) of highly viscous product.

Use of Triethylamine as Described in the Prior Art (EP 0 213 639).

Approx. 179.2 g (0.5 mol) of 2,2'-dihydroxy-3,3'-di-t-butyl-5,5'-dimethoxy-1,1'-biphenyl were added to approx. 1600 ml of toluene. Sufficient toluene was then removed azeotropically in order to remove traces of moisture. The diol-toluene solution was then cooled to 80° C. and approx. 168.7 g (1.67 mol) of triethylamine were added. Approx. 68.7 g (0.5 mol) of $PCl_3$ were added to 200 ml of toluene. To this solution was added dropwise at −10° C. within 1 h and 40 min the diol-toluene solution. The reaction solution was kept at this temperature for a further 30 min. Subsequently, the solution was allowed to warm to room temperature within 2 h. Subsequently, the reaction mixture was filtered to remove the triethylamine hydrochloride precipitate and the precipitate was washed twice with 200 ml of toluene. The filtrate and the wash liquor were combined to give 717.5 g of solution of the phosphorochloridite intermediate in toluene.

Approx. 170 g of further 2,2'-dihydroxy-3,3'-di-t-butyl-5,5'-dimethoxy-1,1'-biphenyl were added to 800 ml of toluene. Subsequently, 48.1 g of triethylamine were added. The 717.5 g of the abovementioned phosphorochloridite-toluene solution were added to the solution at room temperature within 45 min. The temperature was increased to 80° C. for one hour and 45 minutes and then to 95° C. for 2 hours. Subsequently, the mixture was allowed to cool to room temperature. Approx. 600 ml of distilled water were added to the reaction mixture in order to dissolve the solid triethylamine hydrochloride. After the solution had been given time to settle, the phases which formed were separated. The aqueous phase was extracted twice with 250 ml of toluene. The organic phase and the extracts were combined and dried over dried magnesium sulfate for one hour. Subsequently, the solution was filtered and concentrated under reduced pressure to give a solid residue. The residue was recrystallized from acetonitrile and 242.5 g (65.4% of theory) of the diorganophosphite were obtained.

As can be seen with reference to the inventive example, the same yield can be obtained as by the prior art process, although the process is distinctly simpler.

Example 2

Preparation of 2,2'-biphenylphosphorus Chloride of the Formula II

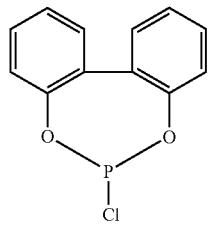

II

Example 2.1

Inventive

To a mixture of 35 g (0.06 mol) of Lewatit MP 62 ion exchanger and 4.13 g=2.62 ml (0.03 mol) of phosphorus trichloride in 150 ml of toluene was added dropwise at room temperature with vigorous stirring a solution of 5.7 g (0.03 mol) of 1,1'-biphenyl-2,2'-diol in 50 ml of toluene. Subsequently, 2 hours of continued reaction time were allowed. For workup, the ion exchanger was filtered off and washing was effected 3 times with 50 ml of dried toluene. The solvent was removed under reduced pressure from the resulting solution. The yield was 7.2 g, 96% of theory. The purity was >95%.

Prior Art

In Phosphoric acid esters of 3,4-Dihydroxytoluene and of 2,2'-Dihydroxybiphenyl. Anschutz, Ludwig; Marquardt, Wolfgang, Chem. Ber. 1956, 89, 1119-23, 48 g of $PCl_3$ were added dropwise within 70 min to 45.7 g of 2,2'-dihydroxybiphenyl in 45 ml of benzene. The 25 mixture was kept under reflux for 5 hours and subsequently at 20° C. for 14 hours. 57% of 2,2'-biphenylenephosphorus chloride were obtained.

U.S. Pat. No. 4,769,498:

Approx. 771.4 g of $PCl_3$ were added dropwise at room temperature to 281.1 g of 1,1'-biphenyl-2,2'-diol, and the mixture was heated (from approx. 22° C. to approx. 83° C.) gradually with stirring and reflux. The reaction mixture was then allowed to cool to approx. 30° C. Subsequently, the mixture was distilled at a vapor temperature of 145° C. in order to remove excess $PCl_3$. A distillate of approx. 468 g was removed overhead. The remaining residue was subsequently distilled at a pressure of 0.5 mmHg and a vapor temperature of from 137 to 140° C. 32.5 g of a yellow, viscous liquid were collected overhead. The vacuum distillation was then continued at a vapor temperature of 143° C. and 270.8 g of a colorless viscous liquid of 1,1'-biphenyl-2,2'-diyl phosphorochloridite were obtained overhead. Although the yield in this case was 72%, it was necessary to work with a 3.7-fold excess of $PCl_3$.

In J. Mol. Catal. A: Chemical 2000, 164, 125-130 a Schlenk tube is provided with 14 mmol of 2,2'-biphenol, 35 ml of toluene and a stirrer, and is subsequently cooled to a temperature of 0° C. To this mixture is added slowly, via a cannula, a mixture of 15 mmol of $PCl_3$, 15 ml of toluene and 5 ml of $Et_3N$. After stirring at ambient temperature overnight, the mixture was filtered with a glass frit. The residue was washed with 50 ml of toluene. The solvent and excess $PCl_3$ were removed from the filtrate by evaporating under reduced pressure. Distillation of the filtrate provided pure product in a yield of 90%.

The process according to the invention has the advantage that a fully amine-free product is obtained and, even as a crude product, can be used further directly. In addition, the yield of 96% is higher than in the other two processes.

Example 3

2,2'-Bis[(1,1'-biphenyl-2,2'-diyl)phosphite]-3,3'-di-tert-butyl-5,5'-dimethoxy-1,1'-biphenyl of the Formula III

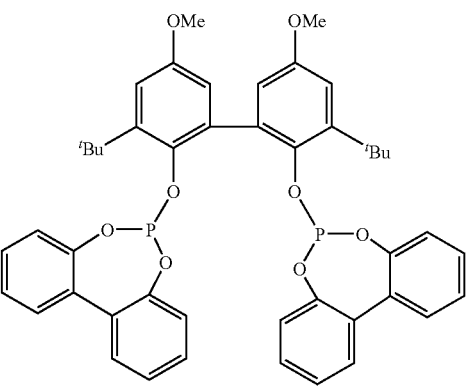

III

Example 3.1

Inventive

To a mixture of 17.5 g (0.03 molar equivalent) of Lewatit MP ion exchanger and 7.2 g (0.029 mol) of 2,2'-biphenylenephosphorus chloride in 100 ml of toluene was added slowly at room temperature a suspension of 4.5 g (0.0125 mol) of 3,3'-di-tert-butyl-2,2'-dihydroxy-5,5'-dimethoxybiphenyl in 100 ml of toluene. Subsequently, the reaction mixture was stirred at room temperature for 2 h and stirred at 60° C. for 2 h. For workup, the ion exchanger was filtered off, toluene was removed under reduced pressure and the resulting residue was recrystallized from hexane. The yield was 7.2 g (50% of theory).

Prior Art Using Triethylamine (WO 95/14659)

To a solution of 1,1'-biphenyl-2,2'-diyl phosphorochloridite (1.40 g, 5.6 mmol) in 0.6 ml of toluene was added at −40° C. within 15 min a solution of 2,2'-dihydroxy-3,3'-di-t-butyl-5,5'-dimethoxy-1,1'-biphenyl (1.00 g, 2.80 mmol) and triethylamine (1.79 ml, 22.4 mmol) in 12 ml of toluene. The resulting mixture was slowly warmed to room temperature overnight. After 6.5 ml of water had been added, the reaction mixture was filtered. The residue was washed repeatedly with water and subsequently dried overnight under reduced pressure. A white solid was obtained and was recrystallized from acetonitrile. 0.72 g of a white powder was obtained (33% yield).

It can be clearly seen that the use of a basic ion exchanger allows a higher yield to be achieved. It is possible in the process according to the invention to dispense with cooling of the reaction mixture or carrying out the reaction at low temperatures, since the reaction proceeds more moderately.

What is claimed is:

1. A process for preparing trivalent organophosphorus compounds by condensing phosphorus compounds of the formula i

(i)

where Hal is a halide selected from chlorine, bromine and iodine and may be the same or different when a plurality of halides are present (a>1), R is an organic radical bonded to the phosphorus via a carbon or oxygen atom, and, when a<2, the R radicals present may be the same or different, and a is a number from 1 to 3, with organic compounds that have at least one OH group, the process comprising carrying out the condensation reaction in the presence of at least one basic ion exchange resin.

2. The process of claim 1, wherein the phosphorus compound of the formula i used is at least one compound selected from the compounds of the following formulae

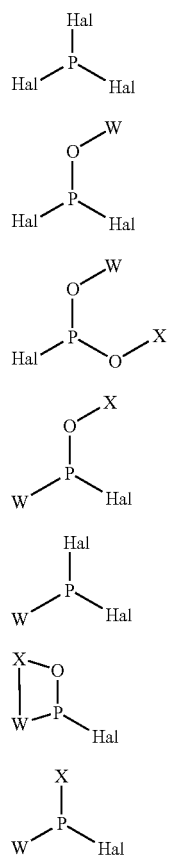

where W and X are substituted or unsubstituted, aliphatic, alicyclic, aliphatic-alicyclic, heterocyclic, aliphatic-heterocyclic, aromatic-aromatic or aliphatic-aromatic hydrocarbons having from 1 to 50 carbon atoms, and W or X are the same or different or covalently joined together.

3. The process of claim 1, wherein the compound used that has at least one hydroxyl group is at least one substituted or unsubstituted compound selected from methanol, ethanol, n-propanol, isopropanol, 1-butanol, 2-butanol, t-butanol, 2-ethylhexanol, isononanol, isodecanol, isotridecanol, phenol, phenol derivatives, 1,4-dihydroxybenzene, 1,2-dihydroxybenzene, 1,8-dihydroxynaphthalene, 1,1'-binaphthyl-2,2'-diol or 2,2'-binaphthyl-1,1'-diol, and the substituted compounds may have substituents selected from primary, secondary and tertiary alkyl groups, alicyclic groups, aromatic groups, —N(R$^5$)$_2$, —NHR$^5$, —NH$_2$, fluorine, chlorine, bromine, iodine, —CN, —C(O)—R$^5$, —C(O)H or —C(O)O—R$^5$, —CF$_3$, —O—R$^5$, —C(O)N—R$^5$, —OC(O)—R$^5$ and/or —Si(R$^5$)$_3$, where R$^5$ is a monovalent hydrocarbon radical, and, when a plurality of hydrocarbon radicals R$^5$ is present, they are the same or different.

4. The process of claim 1, wherein the trivalent organophosphorus compound prepared is at least one compound selected from the compounds of the following formulae

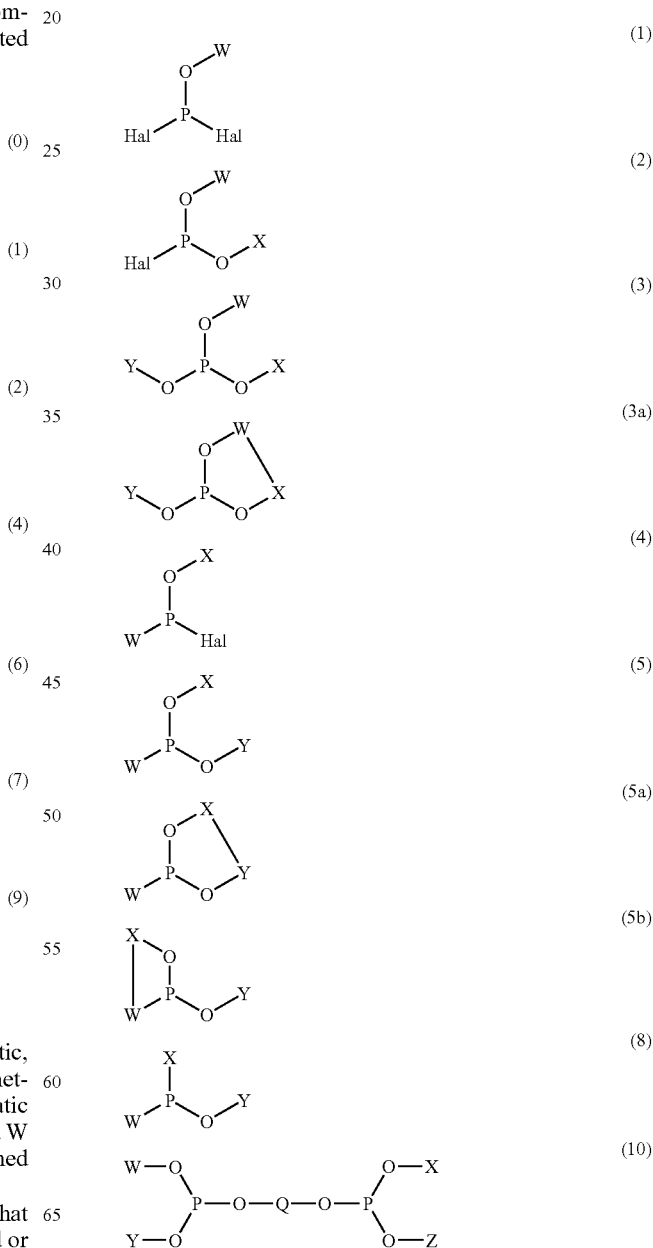

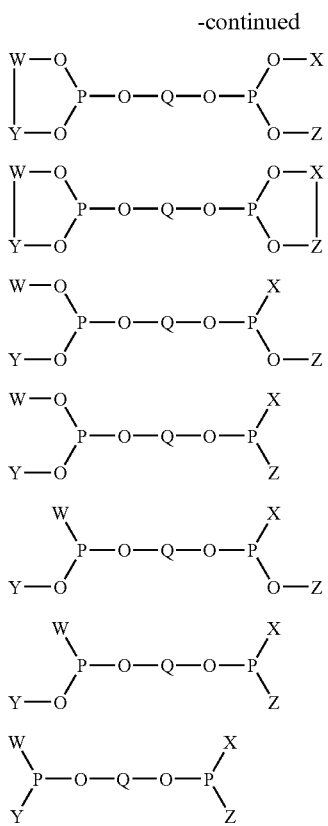

where W, X, Y and Z are each substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, and W, X, Y and Z are the same or different or covalently joined together, and where Q is an at least bivalent, substituted or unsubstituted, aliphatic, alicyclic, aliphatic-alicyclic, heterocyclic, aliphatic-heterocyclic, aromatic, aromatic-aromatic or aliphatic-aromatic hydrocarbon radical.

5. The process of claim 4, wherein the compounds of the formulae (1), (2), (3), (3a), (4), (5), (5a), (5b) or (8) are each prepared by initially charging the phosphorus compound together with one or more basic ion exchange resins and subsequently metering in the compound having an OH group.

6. The process of claim 4, wherein asymmetric diphosphorus compounds are prepared by initially charging the compound having OH groups together with one or more basic ion exchange resins and subsequently metering in the phosphorus compound.

7. The process of claim 1, wherein the reaction of in each case a compound that has at least one phosphorus-halogen bond with a compound having at least one hydroxyl group is one reaction step.

8. The process of claim 7, wherein, when a plurality of reaction steps is carried out, they may be carried out continuously or batchwise.

9. The process of claim 7, wherein, when a plurality of reaction steps is carried out, the same or different ion exchangers are used in the reaction steps.

10. The process of claim 7, wherein, when a plurality of reaction steps is carried out, the same or different temperatures are set in the reaction steps.

11. The process of claim 1, which is carried out in the presence of one or more solvents that are selected from the group of benzene, chlorobenzene, toluene, xylenes, pentane, n-hexane, n-heptane, cyclohexane, methylcyclohexane, diethyl ether, diisopropyl ether, methyl tert-butyl ether, anisole, tetrahydrofuran, 1,4-dioxane, 1,3-dioxolane, ethyl acetate, isobutyl acetate, tert-butyl acetate, ethylene carbonate, propylene carbonate, 1,2-butylene carbonate, acetone, 2-butanone, 3,3-dimethyl-2-butanone, benzonitrile, proprionitrile, acetonitrile, lactones, N-methylpyrrolidone, dimethylformamide, dimethyl sulfoxide, N-alkylmorpholines and sulfolane.

12. The process of claim 1, which is carried out in the presence of polymeric, weakly basic ion exchange resins based on styrene-divinylbenzene copolymers that bear N,N-dialkylamine groups.

13. The process of claim 1, wherein the ion exchanger is used in the form of particles having an average particle size of from 10 μm to 2 mm or in the form of a fixed package.

14. The process of claim 1, wherein the ion exchanger is dried before use in the process.

15. The process of claim 1, which is carried out in the presence of a proton transferrer.

16. The process of claim 1, wherein the at least one basic ion exchange resin is present such that the ratio of moles of acid resulting from the release in moles to moles of free base released by the ion exchange resin is from 1:1 to 3:1.

17. The process of claim 1, wherein the at least one basic ion exchange resin is present such that the ratio of moles of acid resulting from the release in moles to moles of free base released by the ion exchange resin is from 1:1 to 2:1.

* * * * *